United States Patent [19]
Matsumoto et al.

[11] Patent Number: 5,859,297
[45] Date of Patent: Jan. 12, 1999

[54] LABELED REAGENTS FOR USE IN IMMUNOASSAYS AND FLUORESCENT COMPOUNDS AND COMPLEXES USED THEREIN

[75] Inventors: Kazuko Matsumoto, 2578-1-708, Noborito, Tama-ku, Kawasaki-shi, Kanagawa-ken; Jingli Yuan, Tokyo, both of Japan

[73] Assignees: Kazuko Matsumoto, Kawasaki; Suzuki Motor Corporation, Hamamatsu, both of Japan

[21] Appl. No.: 735,517

[22] Filed: Oct. 23, 1996

[30] Foreign Application Priority Data

Aug. 3, 1996 [JP] Japan ................................ 8-051185

[51] Int. Cl.$^6$ .................... C07C 35/08; C07C 331/00; C07D 333/74
[52] U.S. Cl. ..................... 562/828; 562/833; 549/43; 549/57; 549/64; 558/13; 534/15; 534/16; 568/326
[58] Field of Search ...................... 562/828, 835; 568/326; 549/43, 57, 64; 558/13

[56] References Cited

FOREIGN PATENT DOCUMENTS 9216840  1/1992  WIPO .

OTHER PUBLICATIONS

CA 122:209093 (1995).
CA 102:151278 (1984).
Jingli Yuan et al., "Fluorescence Enhancement by Electron-Withdrawing Groups on β–Diektones in EU(III)–β–diketonato–topo Ternary Complexes", *Analytical Sciences*, vol. 12, Feb. 1996, pp. 31–36.

Jingli Yuan et al., "Synthesis of a New Tetradentate β–Diketonate–Europium Chelate That Can Be Covalently Bound to Proteins in Time–Resolved Fluorometry", *Analytical Sciences*, vol. 12, Oct. 1996, pp. 695–699.

*Primary Examiner*—Paul J. Killos
*Attorney, Agent, or Firm*—Bell Seltzer Intellectual Property Law Group of Alston & Bird LLP

[57] ABSTRACT

Disclosed are labeling reagents containing fluorescent compounds represented by the general formula

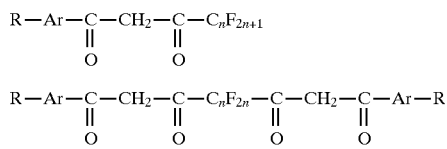

or

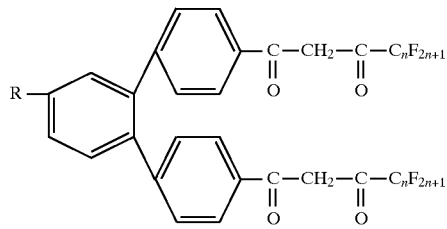

where R is a group capable of combining with proteins, Ar is a conjugated double bond system, and n is a whole number. These labeling reagents have high fluorescence emission intensities, give high synthesis yields, permit both solid-phase measurements and liquid-phase measurements in immunoassays, and require less measuring steps.

9 Claims, 5 Drawing Sheets

● BSA(e)$_{47}$
■ BSA(f)$_{40}$ (e) y=14.234+0.98x   R=1.0
(f) y=14.582+1.01x   R=1.0 y=14.228+0.98x, R=1.0

LABELED REAGENTS FOR USE IN IMMUNOASSAYS AND FLUORESCENT COMPOUNDS AND COMPLEXES USED THEREIN

FIELD OF THE INVENTION AND RELATED ART STATEMENT

This invention relates to labeled reagents for use in time-resolved fluoroimmunoassay and other immunoassay techniques employed in the field of clinical examinations, and to fluorescent compounds and complexes used therein. The term "fluorescent compound" as used herein comprehends any compound that, when it is coordinated to a metal ion to form a complex, can produce fluorescence arising from the complex.

Conventional measuring reagents include β-diketone type (i.e., 2-naphthoyltrifluoroacetone) fluorescent reagents for use in the LKB system and aromatic amine type labeling reagents (BCPDA type labeling reagents).

The labeling reagent used in the LKB system (i.e., an Eu chelate-labeled antibody) cannot produce fluorescence, whether it is used in the free state or in the state combined with a protein such as the antigen. In the LKB system, therefore, the concentration of the antigen is determined by adding a solution of 2-naphthoyltrifluoroacetone, tri-n-octylphosphine oxide and Triton X-100 as an enhancer to liberate Eu(III) in an aqueous solution, and then measuring the fluorescence produced by the resulting Eu(III) chelate micelles.

However, the LKB system has the following disadvantages. First, it is subject to contamination by surroundings (such as serum, reagents and air). Specifically, an excess of the enhancer needs to be added so as to react satisfactorily with Eu(III) liberated in an aqueous solution. Since this excess enhancer reacts with europium present in surroundings (such as air and serum), the concentration of the antigen may be overestimated. Secondly, since the fluorescent compound cannot produce fluorescence in the state combined with a protein such as an antigen or an antibody, the addition of an enhancing reagent is required during the course of the measuring procedure. Moreover, solid-phase measurements are not possible because the fluorescent compound is converted into a form capable of producing fluorescence only in an aqueous solution.

The fluorescent compounds used in the aforesaid aromatic amine type labeling reagents (BCPDA type labeling reagents) include 4,7-bis(chlorosulfophenyl)-1,10-phenanthroline-2,9-dicarboxylic acid (BCPDA), bis(chlorosulfophenyl)phenanthroline-dicarboxylic acid and the like.

However, when an aromatic amine type labeling reagent is used, the fluorescence intensity is as low as 1/100 to 1/200 of that obtained with the LKB system using a β-diketone type reagent (i.e., 2-naphthoyltrifluoroacetone) as described above. Low fluorescence intensities do not permit highly sensitive determination of substances to be assayed. That is, high detection limits prevent measurements down to a low concentration range. In order to enhance fluorescence intensity, an improved multilabeled reagent is disclosed in Japanese Patent Provisional Publication No. 88968/'90. However, this reagent still fails to give a satisfactorily high fluorescence intensity.

Moreover, newly developed β-diketone type labeling reagents are described in Japanese Patent Provisional Publication Nos. 244085/'92 and 10819/'95.

However, the fluorescence intensities obtained with these labeling reagents are as low as about 1.4 times that obtained with the aromatic amine type labeling reagents in which the aforesaid BCPDA is used. Moreover, many steps are required for the synthesis thereof and the yield of the desired compound is low.

Accordingly, it is an object of the present invention to provide labeling reagents which have high fluorescence intensities, are cheaper than aromatic amine type labeling reagents (BCPDA type labeling reagents), give high synthesis yields, permit both solid-phase measurements and liquid-phase measurements, require less measuring steps so as to obtain measured results rapidly, and can be synthesized in a stable form permitting long-term storage, as well as fluorescent compounds and complexes used therein.

SUMMARY OF THE INVENTION

In order to accomplish the above object, the present invention provides fluorescent compounds represented by any of the general formulas

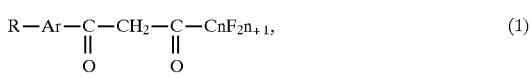

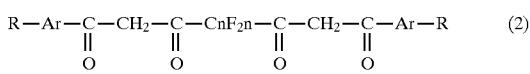

and

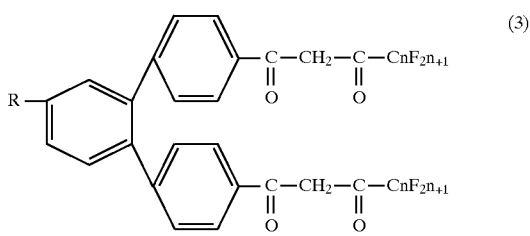

where R is a group capable of combining with proteins, Ar is a conjugated double bond system, and n is a whole number; complexes composed of such fluorescent compounds and lanthanoid metal ions; and labeling reagents for use in immunoassays which contain such fluorescent compounds or such complexes.

The labeling reagents of the present invention can combine directly with proteins to be assayed (such as antigens and antibodies) and can produce fluorescence both in the free state and in the state combined with proteins.

Moreover, the labeling reagents of the present invention have a structure consisting of a β-diketone having attached thereto one or more electron-donating groups (aromatic ring substituent groups) and one or more electron-attracting groups (fluorine-substituted alkyl groups). Accordingly, they produce an intense fluorescence and have a long fluorescence lifetime. Their fluorescence emission intensities are more than about 10 times higher than those of fluorescent reagents used in the LKB system and more than about 1,000 times higher than those of aromatic amine type labeled reagents.

Moreover, the labeling reagents of the present invention can readily be synthesized in high yield. In particular, the pipetting of an enhancing reagent and the third incubation step, which are required in the conventional LKB system, are unnecessary. In addition, the well drying step required in measurements with conventional aromatic amine type labeling reagents is also unnecessary.

Moreover, in contrast to the LKB system, the labeling reagents of the present invention can produce fluorescence without liberating Eu(III) in an aqueous solution.

Consequently, they are not subject to contamination by surroundings. Moreover, they permit the measurement of immune complexes in both the solid phase and the liquid phase.

Furthermore, the labeling reagents of the present invention are stable substances which can be stored for a long period of time, and can be synthesized more cheaply than conventional aromatic amine type labeling reagents.

DETAILED DESCRIPTION OF PREFERRED EMBODIMENTS

Figure 1:
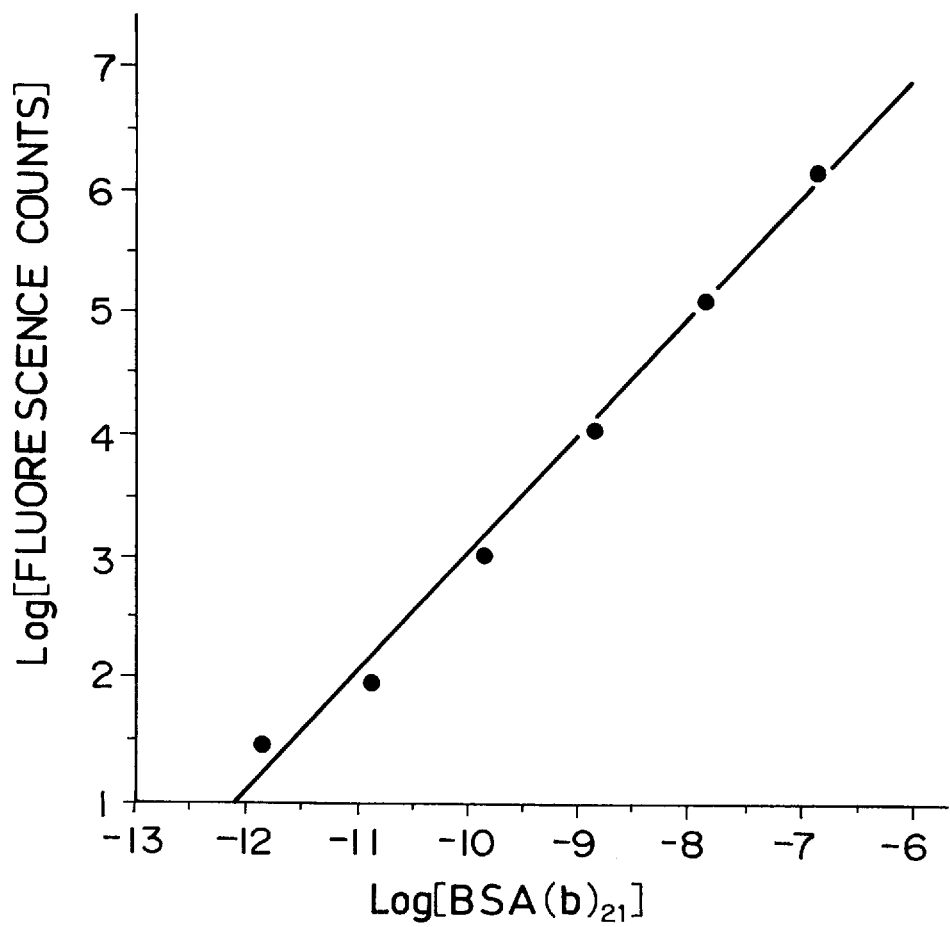
FIG. 1 is a graph in which the logarithm of the concentration (M) of a bovine serum albumin $(b)_{21}$ solution is plotted as abscissa and the logarithm of the fluorescent count as ordinate.

In the above general formula (1), R is a group capable of combining with proteins and so on. Specific examples thereof include the following groups:

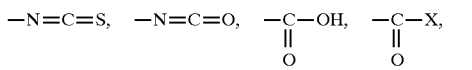
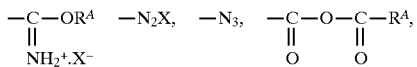
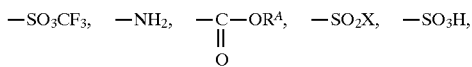
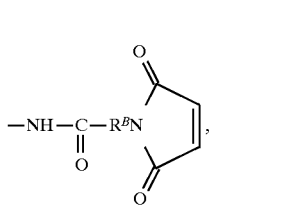
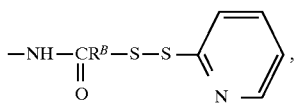
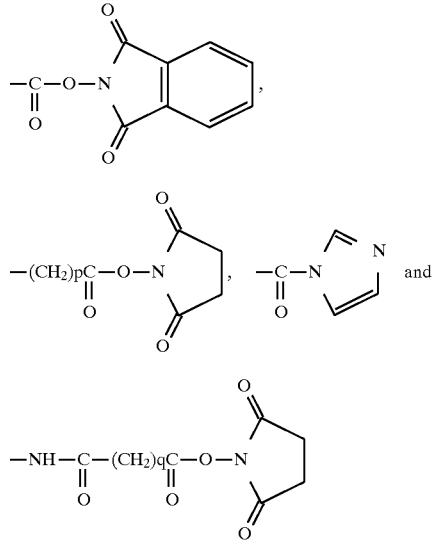

where X is selected from halogen atoms, $-OSO_3CH_3$, $-OSO_2F$, $-OS_2CF_3$, $-SO_2C_4F_9$ and

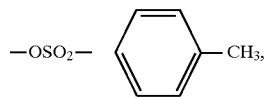

$R^A$ is selected from alkyl, alkenyl, aryl and aralkyl groups, $R^B$ is selected from alkylene, arylene and aralkylene groups, p is a whole number of 0 to 5, and q is a whole number of 2 to 10.

Among them, the chlorosulfonyl group ($-SO_2Cl$) is especially preferred because it has high reactivity with the amino groups of proteins and the like, and can be introduced into fluorescent compounds in a relatively easy way.

Specific examples of proteins and so on which can combine with R in the above general formula (1) include antibodies, biotin-labeled antibodies, antigens, avidin, streptavidin, bovine serum albumin, haptens, hormones, polypeptides, nucleic acids and polynucleotides.

In the above general formula (1), Ar is a conjugated double bond system. Specific examples thereof include aryl groups and the following groups:

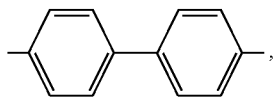
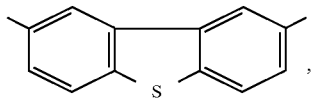
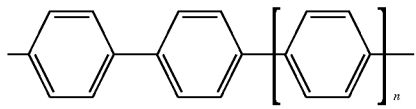
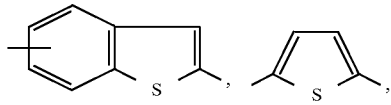

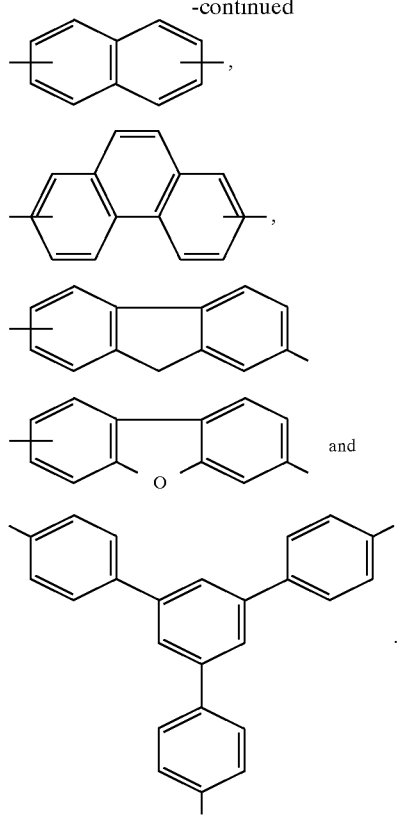

In the above general formula (1), n is a whole number which is usually in the range of 1 to 6.

The lanthanoid metal ions which can be used in the present invention include, for example, ions of europium (Eu), samarium (Sm), terbium (Tb) and dysprosium (Dy).

The fluorescent compounds are synthesized in two steps. The first and seconds steps are separately described below.

First step

A β-diketone compound is synthesized by the Claisen condensation reaction of an acetylated aromatic ring compound with an ethyl perfluorocarboxylate or diethyl perfluorodicarboxylate.

Specific examples of the acetylated aromatic ring compound include 4'-phenylacetophenone, 2-acetyldibenzothiophene (synthesized by the reaction of dibenzothiophene with acetyl chloride), methyl-4,4',4"-terphenyl ketone (synthesized by the reaction of 4,4',4"-terphenyl with acetyl chloride), 2-acetylthiophene, 2-acetylbenzothiophene (synthesized by the reaction of benzothiophene with acetyl chloride) and 4,4'-diacetyl-o-terphenyl (synthesized by the reaction of o-terphenyl with acetyl chloride).

Specific examples of the ethyl perfluorocarboxylate include ethyl trifluoroacetate, ethyl pentafluoropropionate, ethyl heptafluorobutyrate and ethyl perfluoropentanoate.

Specific examples of the diethyl perfluorodicarboxylate include diethyl difluoromalonate, diethyl tetrafluorosuccinate, diethyl hexafluoroglutarate, diethyl perfluoroadipate, diethyl decafluoropimelate and diethyl dodecafluorosuberate.

A schematic diagram showing the synthesis path of the first step is given below. NaOCH$_3$ is a catalyst and dry ether is a solvent. The resulting product is purified by recrystallization. As the solvent for recrystallization, there may be used ethanol, 1,4-dioxane or a mixture thereof.

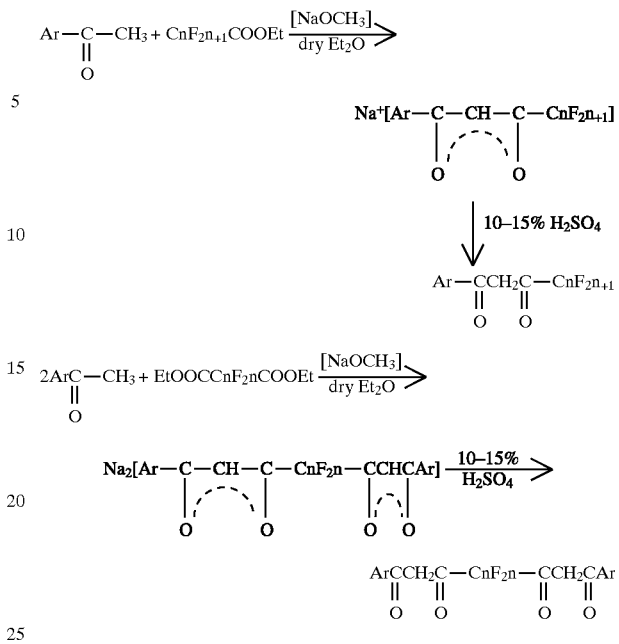

Second step

The chlorosulfonylation reaction of the synthesized β-diketone compound with chlorosulfuric acid is carried out to introduce the chlorosulfonyl group (ClSO$_2$—) into the aromatic ring(s) of the β-diketone molecule. After completion of the reaction of chlorosulfuric acid with the β-diketone, unreacted chlorosulfuric acid is hydrolyzed in cold water. The chlorosulfonylated β-diketone precipitates without dissolving in cold water. A schematic diagram showing the synthesis path of the second step is given below.

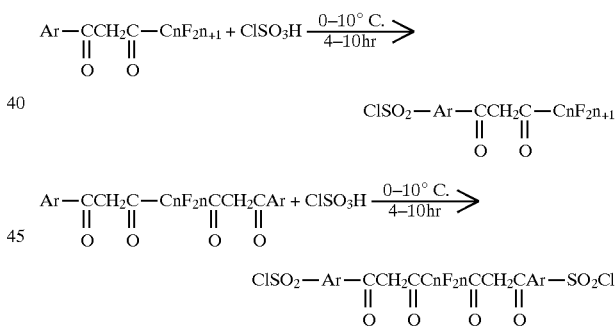

When a fluorescent compound having two chlorosulfonyl groups is directly used in the labeling reaction of a protein, there is a possibility that a polymer-labeled protein will be formed. This can be prevented by protecting any one of the chlorosulfonyl groups prior to labeling. The protection reaction is carried out in DMF or acetonitrile by using NH$_2$CH(CH$_3$)$_2$, C$_6$H$_5$NH$_2$, C$_2$H$_5$NH$_2$ or the like in the presence of N(C$_2$H$_5$)$_3$. This protection reaction is effective in preventing the formation of polymer and thereby increasing the fluorescence intensity of the complex with Eu. However, since it has been reported that fluorescent compounds having similar structures exhibit no polymer formation even when they do not undergo such a protection reaction, it is not necessarily required to subject such fluorescent compounds to a protection reaction.

The fluorescent compounds can be synthesized according to the above-described steps. The labeling of proteins is carried out by an amide-forming reaction between chlorosulfonyl groups and amino groups. This reaction proceeds easily in a carbonate buffer solution (pH 9.0–9.5) at room temperature. A schematic diagram showing the path for the synthesis of labeled proteins is given below.

Protein-NH$_2$+ClSO$_2$—R→Protein-NH—SO$_2$—R

Immunoassays using the labeling reagents of the present invention include, for example, time-resolved fluoroimmunoassay and specific combination assays. Time-resolved fluoroimmunoassay is a highly sensitive fluoroimmunoassay in which a long-life fluorescent label (such as an Eu chelate) is used to measure only the fluorescence signal of the label in a time-resolved fluorometric manner after the background fluorescence having a short lifetime has disappeared. Specific combination assays comprehends immunoassays utilizing an antigen-antibody reaction, assays utilizing a receptor-acceptor combination reaction, assays utilizing the hybridization of nucleic acids, and the like.

EXAMPLES

Preparation of fluorescent compounds (a) to (d)

The method for the preparation of fluorescent compounds represented by the following chemical formulas (a) to (d) is described below.

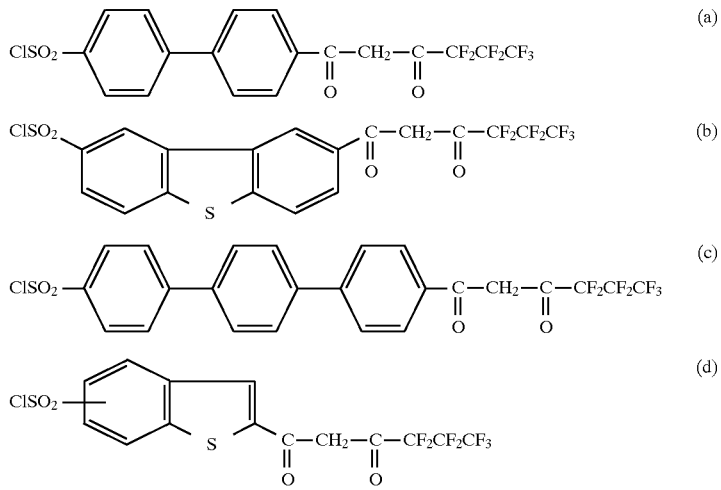

To 40 g of dry ether were added 2.5 g of NaOCH$_3$, 10 mmol of ArCOCH$_3$ (selected from 4'-phenylacetophenone, 2-acetyldibenzothiophene, methyl-4,4',4"-terphenyl ketone and 2-acetylbenzothiophene) and 10 mmol of C$_3$F$_7$COOC$_2$H$_5$. This mixture was sealed at room temperature and stirred for 24 hours. The ether was removed by distillation (or evaporation), and the resulting solid was vacuum-dried for 30 minutes. After the addition of 100 ml of 15% sulfuric acid, the resulting mixture was fully stirred at room temperature for 30 minutes to neutralize the β-diketone sodium salt so formed. The resulting precipitate of β-diketone was separated by suction filtration, washed thoroughly with water, and vacuum-dried for 24 hours. Thereafter, the β-diketone was recrystallized from ethanol. That is, the β-diketone was dissolved in ethanol by heating under reflux, the resulting solution was filtered while hot, and the filtrate was allowed to stand at -20° C. for 24 hours for the purpose of crystallization. The β-diketone crystals so formed were separated by filtration and vacuum-dried at room temperature for 48 hours or more. Thus, the following intermediates (a') to (d') were obtained.

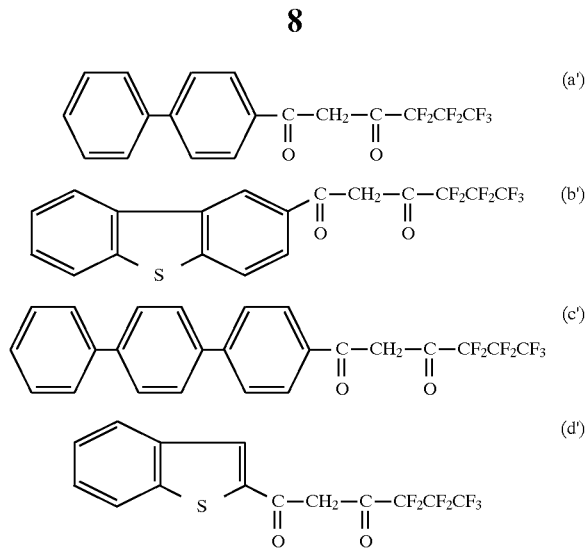

The yields of (a'), (b'), (c') and (d') were 76%, 65%, 82% and 70%, respectively. The results of elemental analysis of (a') to (d') are shown in TABLE 1 below.

TABLE 1

|   | Calcd. (%) | | Found (%) | |
|---|---|---|---|---|
|   | C | H | C | H |
| a' | 55.11 | 2.83 | 55.35 | 2.56 |
| b' | 51.19 | 2.15 | 51.40 | 1.95 |
| c' | 61.54 | 3.23 | 61.60 | 3.11 |
| d' | 49.43 | 2.07 | 49.76 | 1.91 |

Next, 2 mmol of a β-diketone [selected from the aforesaid compounds (a') to (d')] was slowly added to 3 ml of stirred chlorosulfuric acid at 0° C. After this mixture was stirred at 0°–10° C. for 4–10 hours, the reaction mixture was carefully and slowly added dropwise to 80 ml of stirred water/ice (using external cooling with ice/water). The resulting precipitate was quickly separated by centrifugation, washed with cold water (at about 5° C.), and centrifuged twice. Using a small amount of cold water, the precipitate was transferred to a glass filter and freed of water by suction filtration. The chlorosulfonylated β-diketone so formed was vacuum-dried at room temperature for 48 hours or more. The yields of (a), (b), (c) and (d) were 85%, 89%, 91% and 84%, respectively. The results of elemental analysis thereof are shown in TABLE 2.

TABLE 2

|   | Calcd. (%) | | Found (%) | |
|---|---|---|---|---|
|   | C | H | C | H |
| a | 42.49 | 2.38 | 42.20 | 2.47 |
| b | 41.51 | 1.55 | 41.04 | 1.48 |
| c | 50.85 | 2.49 | 50.40 | 2.31 |
| d | 35.72 | 1.28 | 35.40 | 1.06 |

Labeling of a protein with fluorescent compound (b)

The labeling of bovine serum albumin with the aforesaid fluorescent compound (b) is described below.

First of all, 50 mg of bovine serum albumin (hereinafter abbreviated as "BSA") was dissolved in 8 ml of a 0.1 mol/L carbonate buffer solution (pH 9.3). Then, 2 ml of a DMF solution containing the aforesaid fluorescent compound (b) in the same molar amount as the amino groups present in bovine serum albumin (59 —$NH_2$ groups per molecule) was slowly added dropwise to the stirred BSA solution at room temperature. After this mixture was stirred at room temperature for an hour, the labeled BSA and the hydrolyzate of unreacted fluorescent compound were separated by gel filtration. In this separation step using a gel column (Sephadex G-50, 1.0×29.1 cm), a 0.05 mol/L aqueous solution of ammonium hydrogen carbonate (pH 8.0) was used as the developing solvent. The flow rate was 1 ml per 90 seconds and the effluent was collected as 1 ml fractions. Since a satisfactory separating effect would not be achieved by separating 10 ml of the solution at a time under these column conditions, 5 ml portions of the solution were separated by two columns. Fractions containing the labeled BSA were combined and dialyzed against water at 4° C. overnight to remove inorganic salts therefrom. Using the solution before gel filtration, its absorbance at 330 nm was measured. Then, the molar absorption coefficient at 330 nm of the fluorescent compound used was calculated from the molar concentration of the fluorescent compound used and the absorbance at 330 nm. The molar absorption coefficient so calculated was $1.8 \times 10^4$ $mol^{-1}$ $cm^{-1}$ L, and there was no absorption of bovine serum albumin at 330 nm. On the assumption that the molar absorption coefficient does not change during the process of the labeling reaction, the label concentration in the labeled BSA solution and the combination ratio of BSA to label were calculated. The combination ratio of BSA to the fluorescent compound in the labeled BSA fraction obtained in the above-described manner was about 20. This labeled BSA is referred to as "$BSA(label)_{20}$".

Method for the measurement of fluorescence intensities and results

Fluorometric measurements were made with a Hitachi F-4500 fluorescence spectrophotometer (manufactured by Hitachi Ltd.) using a 150 W xenon lamp as the excitation light source. Prior to measurements, the spectral characteristics of the excitation side spectrometer (200 to 600 nm) and the like were corrected by using Rhodamine B as a light quantum meter, and the spectral characteristics of the fluorescence side spectrometer (200 to 600 nm), the spectral characteristics of the detector, and the like were corrected by using a diffusion element. Fluorescence lifetimes were measured with an instrument consisting of the combination of an LPX100 Excimer Laser pulsed light source (pulse half-width <10 ns, 10 Hz; manufactured by Lambda Physik) and an HR320 spectrometer (manufactured by SPEX). Specifically, changes in fluorescence intensity attending changes in delay time were measured and the fluorescence lifetime τ was calculated according to the following equation.

$$\ln I(t) = \ln I(0) - t/\tau$$

Time-resolved fluorometric measurements were made with a Cyber Fluor 615 time-resolved fluorophotometer, and samples were excited with a 337.1 mm nitrogen laser to measure fluorescence intensities at 615 nm. The measuring conditions included a delay time of 200 μs and counting times of 200 to 600 μs. The measuring wells comprised white opaque polystyrene wells (manufactured by Dynatech Laboratories).

Each fluorescent compound was dissolved in an organic solvent such as acetone, methanol or ethanol. Then, using an $EuCl_3$ solution, fluorescent compound–$Eu^{3+}$ standard solutions were prepared and their fluorescence intensities were measured. The results thus obtained are shown in TABLE 3.

TABLE 3

| Fluorescent compound | $\lambda_{ex}$ (nm) | $\lambda_{em}$ (nm) | Fluorescence intensity ($10^3$ $cm^{-1}$$m^{-1}$) |
|---|---|---|---|
| LKB system (conventional technique) | 339 | 610 | 12.16 |
| a' | 360 | 610 | About 120 |
| b' | 360 | 610 | About 120 |
| c' | 360 | 610 | About 120 |
| d' | 360 | 610 | About 120 |

Fluorescence characteristics of a labeled BSA solution in the presence of europium(III)

The addition of an $EuCl_3$ solution to a β-diketone-labeled BSA solution yields an intensely fluorescent solution. Using a $BSA(b)_{21}$–$Eu^{3+}$ solution so prepared, its fluorescence spectrum, the influence of pH and buffer solutions on its fluorescence intensity, and its fluorescence lifetime were measured.

The fluorescence spectrum of the $BSA(b)_{21}$–$Eu^{3+}$ solution was as follows.

In Tris-HCl: $\lambda_{ex.max}$=253 nm, 331 nm
$\lambda_{em.\ max}$=612 nm

In topo-SDS-$NaHCO_3$: $\lambda_{ex.\ max}$=253 nm, 339 nm
λem.max=614 nm

The results of measurement of the influence of pH and buffer solutions on the fluorescence intensity of the BSA $(b)_{21}$–$Eu^{3+}$ solution and of its fluorescence lifetime are shown in TABLE 4.

TABLE 4

| Buffer solution | 0.1 mol/L Tris-HCl | | | | | 0.1 mol/L carbonate | 0.1 mol/L phosphate | $1.0 \times 10^{-5}$ mol/L topo-0.05% SDS-0.1 mol/L NaHCO$_3$ |
|---|---|---|---|---|---|---|---|---|
| pH | 7.2 | 7.8 | 8.5 | 9.1 | 9.9 | 9.3 | 9.0 | 8.4 |
| Relative fluorescence intensity | 62 | 77 | 90 | 96 | 100 | 49 | 27 | 250 |
| Fluorescence lifetime | | | 300 μs | | | | | 425 μs |

*$\lambda_{ex}$ = 337 nm.
Measured solution: BSA(b)$_{21}$-Eu$^{3+}$, [BSA(b)$_{21}$] = $1.5 \times 10^{-7}$ mol/L, [Eu$^{3+}$] = $5.0 \times 10^{-6}$ mol/L.

It can be seen from TABLE 4 that the fluorescent intensity depends on the pH of the solution and the composition of the buffer solution. An intense fluorescence was produced in a Tris-HCl solution. The fluorescence was relatively weaker in a carbonate buffer solution and significantly weaker in a phosphate buffer solution. Moreover, in a solution of topo having high coordination power to Eu$^{3+}$, the fluorescence was much more intense owing to the powerful "synergic effect" of topo. At the same time, a slight increase in fluorescence lifetime was observed. It was confirmed by experiment that the fluorescence of the solution was not affected by the oxygen dissolved therein.

Time-resolved fluorometry of labeled BSA solutions

Using a BSA(b)$_{21}$ solution obtained as above, a $1.0 \times 10^{-5}$ mol/L topo–0.05% SDS-0.1 mol/L NaCHO$_3$ solution, and a $1.0 \times 10^{-5}$ mol/L EuCl$_3$ solution, a BSA(b)$_{21}$–Eu$^{3+}$ standard solution ($4.24 \times 10^{-14}$ mol/L) was prepared. At the same time, a series of solutions were prepared by fixing the Eu$^{3+}$ concentration at $1.0 \times 10^{-6}$ mol/L and varying the BSA(b)$_{21}$ concentration. The prepared solutions were allowed to stand at room temperature for 2 hours and then subjected to time-resolved fluorometry. Measurements were made by pipetting each solution (having an identical concentration) into 4 wells (300 μl per well), and the average of the measured values was regarded as the measured value (I). Similarly, the solvent was pipetted into 4 wells and the average of the measured values was regarded as the background ($I_0$). The (I–$I_0$) values thus obtained were used as fluorescent counts to construct a working curve. The results are shown in FIG. 1.

From FIG. 1, the detection limit of fluorescent compound (b) was determined to be $8.9 \times 10^{-12}$ mol/L.

Using a time-resolved fluorophotometer ("Cyber Fluor 615"), the detection sensitivity of the labeled reagent of the present invention (i.e., the labeled BSA-Eu$^{3+}$) was compared with those of conventional techniques (i.e., the LKB system and an aromatic amine type labeled reagent). It can be seen from TABLE 5 that the fluorescent compound of the present invention is 5 times as sensitive as the LKB system and about 1,000 times as sensitive as BCPDA (or the aromatic amine type labeled reagent).

TABLE 5

| | Detection limit of fluorescent compound (mol/L) |
|---|---|
| LKB system | $5.0 \times 10^{-11}$ |
| BCPDA | $1.0 \times 10^{-8}$ |
| b | $8.9 \times 10^{-12}$ |

Preparation of fluorescent compounds (e) to (i)

The method for the preparation of fluorescent compounds represented by the following chemical formulas (e) to (i) is described below.

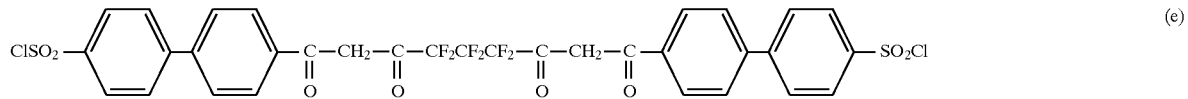

(e)

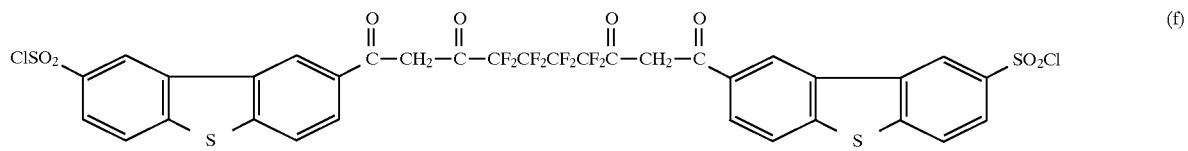

(f)

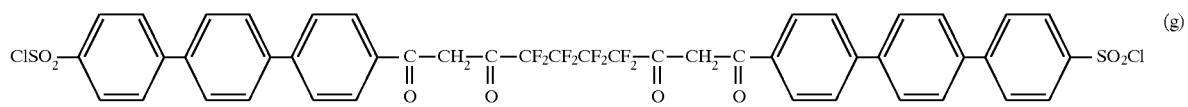

(g)

-continued

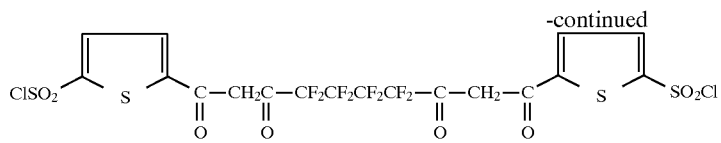
(h)

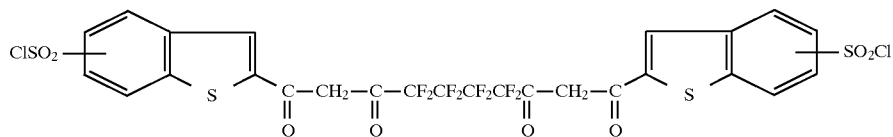
(i)

To 50 g of dry ether were added 3.0 g of NaOCH$_3$, 20 mmol of ArCOCH$_3$ (selected from 4'-phenylacetophenone, 2-acetyldibenzothiophene, methyl-4,4',4"-terphenyl ketone, 2-acetylthiophene and 2-acetylbenzothiophene) and 10 mmol of C$_2$H$_5$OOCC$_4$F$_8$COOC$_2$H$_5$. This mixture was sealed at room temperature and stirred for 24 hours. The ether was removed by distillation (or evaporation), and the resulting solid was vacuum-dried for 30 minutes. After the addition of 100 ml of 15% sulfuric acid, the resulting mixture was fully stirred at room temperature for 30 minutes to neutralize the β-diketone sodium salt so formed. The resulting precipitate of β-diketone was separated by suction filtration, washed thoroughly with water, and vacuum-dried for 24 hours. Thereafter, the β-diketone was recrystallized from a 5:1 mixture of ethanol and 1,4-dioxane (when 4'-phenylacetophenone or methyl-4,4',4"-terphenyl ketone was used), 1,4-dioxane (when 2-acetyldibenzothiophene was used) or ethanol (when 2-acetylthiophene or 2-acetylbenzothiophene was used). The β-diketone crystals so formed were separated by filtration and vacuum-dried at room temperature for 48 hours or more. Thus, the following intermediates (e') to (i') were obtained.

TABLE 6

|   | Calcd. (%) | | Found (%) | |
|---|---|---|---|---|
|   | C | H | C | H |
| e' | 63.16 | 3.43 | 63.70 | 3.15 |
| f' | 57.79 | 2.57 | 57.62 | 2.51 |
| g' | 69.17 | 3.78 | 69.45 | 3.52 |
| h' | 42.69 | 1.99 | 42.56 | 2.04 |
| i' | 51.49 | 2.33 | 51.78 | 2.10 |

Next, 2 mmol of a β-diketone [selected from the aforesaid compounds (e') to (i')] was slowly added to 5 ml of stirred chlorosulfuric acid at 0° C. After this mixture was stirred at 0°–10° C. for 4–10 hours, the reaction mixture was carefully and slowly added dropwise to 120 ml of stirred water/ice (using external cooling with ice/water). The resulting precipitate was quickly separated by centrifugation, washed with cold water (at about 5° C.), and centrifuged twice. Using a small amount of cold water, the precipitate was transferred to a glass filter and freed of water by suction filtration. However, since the amount of the precipitate of (h)

(e')

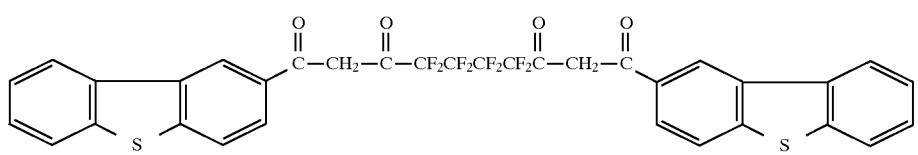
(f')

(g')

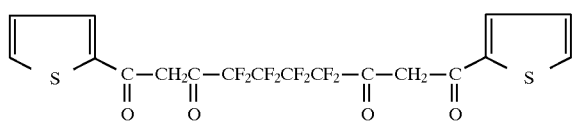
(h')

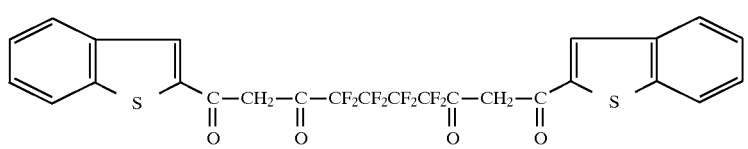
(i')

The yields of (e'), (f'), (g'), (h') and (i') were 65%, 50%, 71%, 79% and 69%, respectively. The results of elemental analysis of (e') to (i') are shown in TABLE 6 below.

was very small, this precipitate was treated solely by centrifuging it twice and discarding the supernatant. The chlorosulfonylated β-diketone so formed was vacuum-dried at room temperature for 48 hours or more. The yields of (e), (f), (g), (h) and (i) were 85%, 86%, 89%, 30% and 80%, respectively. The results of elemental analysis thereof are shown in TABLE 7 below.

TABLE 7

|   | Calcd. (%) | | Found (%) | |
|---|---|---|---|---|
|   | C | H | C | H |
| e | 46.43 | 2.75 | 46.29 | 2.40 |
| f | 42.64 | 2.31 | 42.38 | 1.95 |
| g | 53.55 | 3.13 | 53.21 | 2.91 |
| h | 28.54 | 1.86 | 28.14 | 1.67 |
| i | 37.20 | 1.92 | 36.98 | 1.69 |

Labeling of a protein with fluorescent compound (e)

The labeling of bovine serum albumin with the aforesaid fluorescent compound (e) is described below.

1.00 ml of a DMF solution containing 0.128 mol/L of $NH_2CH(CH_3)_2$ and 0.150 mol/L of $N(C_2H_5)_3$ was added dropwise to a stirred solution of 75.3 mg (0.0856 mmol) of the aforesaid compound (e) in 1.00 ml of dry DMF. After this DMF solution was stirred at room temperature for 20–30 minutes, it was slowly added dropwise to a stirred solution of 50 mg of BSA in 10 ml of a 0.1 mol/L carbonate buffer solution (pH 9.30). After this mixture was stirred at room temperature for an hour, the labeled BSA and the hydrolyzate of unreacted fluorescent compound were separated by gel filtration. In this separation step using a gel column (Sephadex G-50, 1.0×29.1 cm), a 0.05 mol/L aqueous solution of ammonium hydrogen carbonate (pH 8.0) was used as the developing solvent. The flow rate was 1 ml per 90 seconds and the effluent was collected as 1 ml fractions. Since a satisfactory separating effect would not be achieved by separating 10 ml of the solution at a time under these column conditions, 3 ml portions of the solution were separated. Fractions containing the labeled BSA were combined and dialyzed against water at 4° C. overnight to remove inorganic salts therefrom. Using the solution before gel filtration, its absorbance at 330 nm was measured. Then, the molar absorption coefficient at 330 nm of BSA was calculated from the molar concentration of BSA used and the absorbance at 330 nm. The molar absorption coefficient so calculated was $3.65 \times 10^4$ $mol^{-1}$ $cm^{-1}$ L. The labeling ratio of BSA to the fluorescent compound in the labeled BSA fraction was about 26.

BSA(fluorescent compound)$_n$ solutions having higher labeling ratios were obtained by carrying out the above-described reaction while increasing the amount of the fluorescent compound and the concentration of the DMF solution containing $NH_2CH(CH_3)_2$ and $N(C_2H_5)_3$. When the amount of the fluorescent compound was 263.9 mg and a DMF solution containing 0.342 mol/L of $NH_2CH(CH3)_2$ and 0.50 mol/L of $N(C_2H_5)_3$ was used, there was obtained a solution having the highest labeling ratio of 47.

Labeling of avidin and streptoavidin with fluorescent compound (e)

The labeling of avidin (AD) and streptoavidin (SA) with the aforesaid fluorescent compound (e) is described below.

250 μL of an acetonitrile solution containing 0.072 mol/L of $NH_2CH(CH_3)_2$ and 0.10 mol/L of $N(C_2H_5)_3$ was added dropwise to a stirred solution of 11.8 mg (0.013 mmol) of the aforesaid compound (e) in 250 μL of acetonitrile. After this solution was stirred at room temperature for 30 minutes, the acetonitrile solvent was evaporated in a stream of dry nitrogen gas. Thereafter, a solution of 5 mg of avidin (or streptoavidin) in 1.1 ml of a 0.1 mol/L carbonate buffer solution (pH 9.1) and 25 μL of DMF was added thereto. After this mixture was stirred at room temperature for two hours, the insoluble matter was separated by centrifugation. The precipitate was washed with 2.0 ml of a 0.05 mol/L Tris-HCl buffer solution (pH 7.7) and centrifuged. The two supernatants were combined and dialyzed twice against 4 L of a solution containing 0.1 mol/L of $NaHCO_3$ and 0.25 g of $NaN_3$ at 4° C. (for 16 hours and for 6 hours, respectively). The labeling ratio of protein to the fluorescent compound in the labeled protein solution obtained in this manner was about 8.

The above-described procedure is also applicable to the labeling of proteins such as antibodies. The labeled avidin and the labeled streptoavidin can be directly applied to immunoassays based on the avidin-biotin reaction with biotin-labeled antibodies, antigens, DNA and the like.

Method for the measurement of fluorescence intensities and results

The method for the measurement of fluorescence intensities was the same as described above for fluorescent compound (b). The results are shown in TABLE 8.

TABLE 8

| Fluorescent compound | $\lambda_{ex}$ (nm) | $\lambda_{em}$ (nm) | Fluorescence intensity ($10^3$ $cm^{-1}m^{-1}$) |
|---|---|---|---|
| LKB system (conventional technique) | 339 | 610 | 12.16 |
| e' | 360 | 610 | About 150 |
| f' | 360 | 610 | About 150 |
| g' | 360 | 610 | About 150 |
| h' | 360 | 610 | About 150 |
| i' | 360 | 610 | About 150 |

Fluorescence characteristics of a labeled BSA solution in the presence of europium(III)

The addition of an $EuCl_3$ solution to a β-diketone-labeled BSA solution yields an intensely fluorescent solution. Using the aforesaid compound (e) as a fluorescent compound, the fluorescence spectrum of a BSA(e)$_n$–$Eu^{3+}$ solution, the influence of pH and buffer solutions on its fluorescence intensity, and its fluorescence lifetime were measured.

The fluorescence spectrum of the BSA(e)$_n$–$Eu^{3+}$ solution was as follows.

In Tris-HCl: $\lambda_{ex.max}$=336 nm
$\lambda_{em.max}$=611.6 nm (half-width, about 9 nm)
In carbonate buffer solution:
$\lambda_{ex.max}$=330 nm
$\lambda_{em.max}$611.2 nm (half-width, about 9 nm)
In topo-SDS-$NaHCO_3$*:
$\lambda_{ex.max}$=341 nm
$\lambda_{em.max}$=613.6 nm (half-width, about 9 nm)
(* A $1.0 \times 10^{-5}$ mol/L topo–0.05% SDS–0.1 mol/L $NaHCO_3$ solution)

The shape of the fluorescence spectrum remain unchanged even if the labeling ratio (n) is varied.

The results of measurement of the influence of pH and buffer solutions on the fluorescence intensity of the BSA(e)$_n$–$Eu^{3+}$ solution and of its fluorescence lifetime are shown in TABLE 9. In TABLE 9, the fluorescence intensities of various solutions are expressed as relative values based on the fluorescence intensity (or count) of a 0.1 mol/L Tris-HCl solution (pH 9.1). These relative fluorescence intensities remain unchanged even if the labeling ratio (n) is varied.

TABLE 9

| Buffer solution | 0.1 mol/L Tris-HCl | | | | 0.1 mol/L carbonate | 0.1 mol/L phosphate | $1.0 \times 10^{-5}$ mol/L topo-0.05% SDS-0.1 mol/L NaHCO$_3$ |
|---|---|---|---|---|---|---|---|
| pH | 7.2 7.8 8.5 9.1 | | | 9.9 | 9.3 | 9.0 | 8.4 |
| Relative fluorescence intensity | 70 75 88 100 | | | 100 | 61 | 3 | 508 |
| Fluorescence lifetime | 2600 $\mu$s | | | | | | 290 $\mu$s |

*$\lambda_{ex}$ = 337 nm.
Measured solution: BSA(e)$_{30}$-Eu$^{3+}$, [BSA(e)$_{30}$] = 1.8 × 10$^{-8}$ mol/L, [Eu$^{3+}$] = 1.0 × 10$^{-6}$ mol/L.

Next, using the aforesaid compound (f) as a fluorescent compound, the fluorescence spectrum of a BSA(f)$_n$–Eu$^{3+}$ solution, the influence of pH and buffer solutions on its fluorescence intensity, and its fluorescence lifetime were measured. The fluorescence spectrum of the BSA(f)$_n$–Eu$^{3+}$ solution was as follows.

In Tris-HCl: $\lambda_{ex.max}$=253 nm, 339 nm
$\lambda$em.max=612 nm (half-width, about 9 nm)
In carbonate buffer solution:
$\lambda_{ex.max}$=253 nm, 330 nm
$\lambda_{em.max}$=611.6 nm (half-width, about 9 nm)
In phosphate buffer solution:
$\lambda_{ex.max}$=253 nm, 332 nm
$\lambda_{em.max}$=611.6 nm (half-width, about 9 nm)
In topo-SDS-NaHCO$_3$*:
$\lambda_{ex.max}$=253 nm, 341 nm
$\lambda_{em.max}$=613.5 nm (half-width, about 9 nm)
(* A 1.0×10$^{-5}$ mol/L topo-0.05% SDS-0.1 mol/L NaHCO$_3$ solution)

The shape of the fluorescence spectrum remain unchanged even if the labeling ratio (n) is varied.

The results of measurement of the influence of pH and buffer solutions on the fluorescence intensity of the BSA(f)$_n$–Eu$^{3+}$ solution and of its fluorescence lifetime are shown in TABLE 10. In TABLE 10, the fluorescence intensities of various solutions are expressed as relative values based on the fluorescence intensity (or count) of a 0.1 mol/L Tris-HCl solution (pH 9.1). These relative fluorescence intensities remain unchanged even if the labeling ratio (n) is varied.

TABLE 10

| Buffer solution | 0.1 mol/L Tris-HCl | | | | 0.1 mol/L carbon-ate | 0.1 mol/L phos-phate | $1.0 \times 10^{-5}$ mol/L topo-0.05% SDS-0.1 mol/L NaHCO$_3$ |
|---|---|---|---|---|---|---|---|
| pH | 7.2 7.8 8.5 9.1 | | | 9.9 | 9.3 | 9.0 | 8.4 |
| Relative fluorescence intensity | 54 72 92 100 | | | 89 | 76 | 37 | 621 |
| Fluorescence lifetime | 227 $\mu$s | | | | | | 240 $\mu$s |

*$\lambda_{ex}$ = 337 nm.
Measured solution: BSA(f)$_{40}$-Eu$^{3+}$, [BSA(f)$_{40}$] = 2.2 × 10$^{-8}$ mol/L, [Eu$^{3+}$] = 1.0 × 10$^{-6}$ mol/L.

It can be seen from the results shown in TABLEs 9 and 10 that the fluorescent intensity depends on the pH of the solution and the composition of the buffer solution. An intense fluorescence was produced in a Tris-HCl solution. The fluorescence was relatively weaker in a carbonate buffer solution and significantly weaker in a phosphate buffer solution. Moreover, in a solution of topo having high coordination power to Eu$^{3+}$, the fluorescence was much more intense owing to the powerful "synergic effect" of topo. At the same time, a slight increase in fluorescence lifetime was observed. It was confirmed by experiment that the fluorescence of the solution was not affected by the oxygen dissolved therein.

Time-resolved fluorometry of labeled BSA solutions

Figure 2:
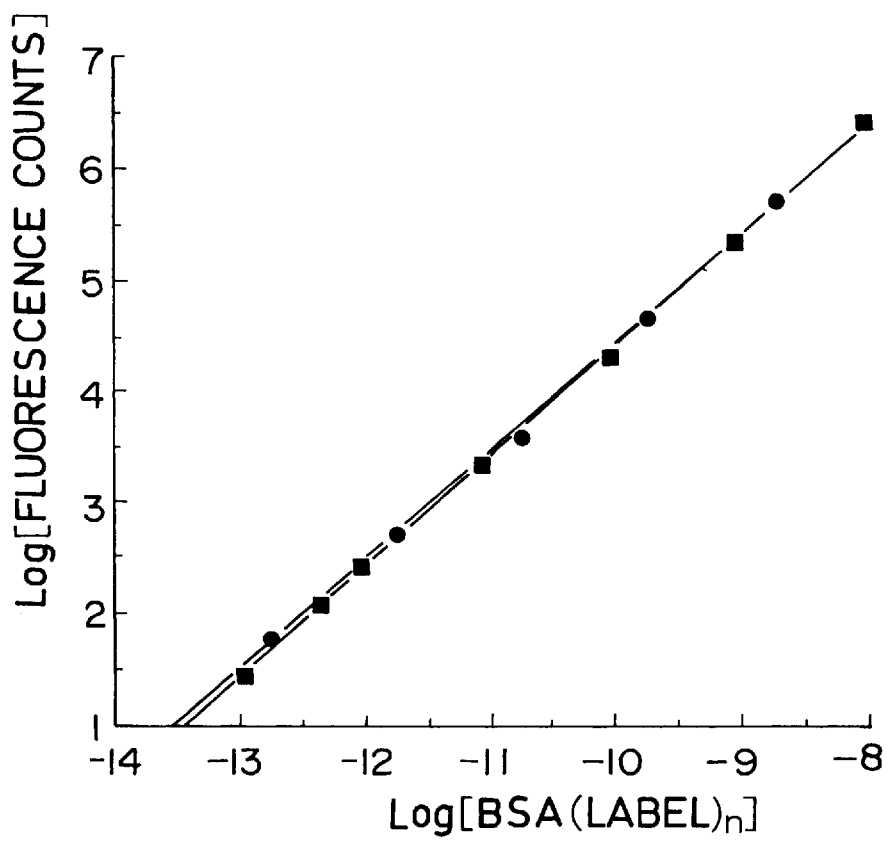
FIG. 2 is a graph in which the logarithm of the concentration (M) of a bovine serum albumin $(e)_{47}$ solution or a bovine serum albumin $(f)_{40}$ solution is plotted as abscissa and the logarithm of the fluorescent count as ordinate.

Using a BSA(e)$_{47}$ or BSA(f)$_{40}$ solution obtained as above, a 1.0×10$^{-5}$ mol/L topo-0.05% SDS-0.1 mol/L NaHCO$_3$ solution, and a 1.0×10$^{-5}$ mol/L EuCl$_3$ solution, BSA (fluorescent compound)$_n$–Eu$^{3+}$ standard solutions (1.6×10$^{-14}$ mol/L for the BSA(e)$_{47}$ solution and 9.3×10$^{-14}$ mol/L for the BSA(f)$_{40}$ solution) were prepared. At the same time, a series of solutions were prepared by fixing the Eu$^{3+}$ concentration at 1.0×10$^{-6}$ mol/L and varying the BSA (fluorescent compound)$_n$ concentration. The prepared solutions were allowed to stand at room temperature for 2 hours and then subjected to time-resolved fluorometry. Measurements were made by pipetting each solution (having an identical concentration) into 4 wells (300 $\mu$l per well), and the average of the measured values was regarded as the measured value (I). Similarly, the solvent was pipetted into 4 wells and the average of the measured values was regarded as the background (I$_0$). The (I–I$_0$) values thus obtained were used as fluorescent counts to construct a working curve. The results are shown in FIG. 2. From FIG. 2, the detection limits of fluorescent compounds (e) and (f) were determined to be 7.5×10$^{-13}$ mol/L and 3.7×10$^{-12}$ mol/L.

Using a time-resolved fluorophotometer ("Cyber Fluor 615"), the detection sensitivities of the labeled reagents of the present invention (i.e., the labeled BSA–Eu$^{3+}$) were compared with those of conventional techniques (i.e., the LKB system and an aromatic amine type labeled reagent). It can be seen from TABLE 11 that the labeled reagents of the present invention are several tens of times as sensitive as the LKB system and about 2,000 or more times as sensitive as the aromatic amine type labeled reagent using BCPDA as the fluorescent compound.

TABLE 11

| | Detection limit of fluorescent compound (mol/L) |
|---|---|
| LKB system | 5.0 × 10$^{-11}$ |
| BCPDA | 1.0 × 10$^{-8}$ |
| e | 7.5 × 10$^{-13}$ |
| f | 3.7 × 10$^{-12}$ |

Synthesis of 4,4'-diacetyl-o-terphenyl

An example using 4,4'-diacetyl-o-terphenyl as an acetylated aromatic ring compound is given below. First of all, the method for the synthesis of 4,4'-diacetyl-o-terphenyl is described.

A solution of 100 mmol of o-terphenyl in 100 ml of $CH_2Cl_2$ was slowly added dropwise to a stirred solution of 210 mmol of $AlCl_3$ and 205 mmol of $CH_3COCl$ in 200 ml of $CH_2Cl_2$ at 0° C. This mixture was stirred at 0° C. for 30 minutes and then at room temperature for 24 hours. The reaction mixture was further refluxed for 2 hours and poured into ice/hydrochloric acid (conc.). After this mixture was fully stirred, $CH_2Cl_2$ was removed by vacuum distillation. The precipitate was separated by filtration and washed thoroughly with water. The product was recrystallized from about 250 ml of 2-butanone, and the needle crystals so formed were separated by filtration and vacuum-dried. Thus, 22.1 g of the product was obtained in a 70.3% yield. The results of elemental analysis were as follows:

Elemental analysis: Calcd. (%): C, 84.05; H, 5.77. Found (%): C, 84.06; H, 5.87.

It was confirmed by $^1$H-NMR that the product was the desired compound.

Synthesis of intermediate (j') of fluorescent compound (j)

The method for the synthesis of the following compound (j')

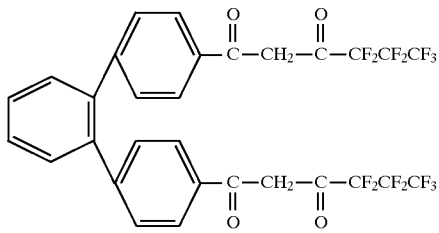

which is an intermediate for the preparation of fluorescent compound (j) represented by the following formula

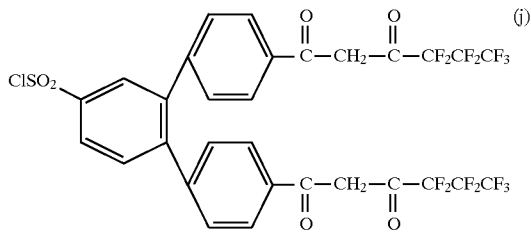

is described below.

To 30 g of dry ether ($Et_2O$) were added 3.0 g of $NaOCH_3$, 10 mmol of 4,4'-diacetyl-o-terphenyl and 20 mmol of $C_3F_7COOC_2H_5$. This mixture was sealed at room temperature and stirred for 24 hours. The dry ether was removed by distillation (or evaporation), and the resulting solid was vacuum-dried for 30 minutes. After the product was neutralized with 100 ml of 15% sulfuric acid, the resulting precipitate was separated by filtration and washed thoroughly with water. The precipitate was dissolved in 200 ml of ethanol by the application of heat, and the resulting solution was filtered to remove insoluble matter therefrom. This solution was concentrated under reduced pressure to about 20 ml, and slowly added dropwise to 200 ml of stirred petroleum ether. After this mixture was fully stirred, the small amount of precipitate so formed was removed by filtration and the filtrate was concentrated under reduced pressure to remove all organic solvent therefrom. The resulting oil was vacuum-dried to obtain a yellow powder. This yellow powder was thoroughly washed with petroleum ether and then vacuum-dried for 24 hours. Thus, 4.60 g of the product was obtained in a 65.0% yield.

Elemental analysis: Calcd. (%): C, 51.00; H, 2.28. Found (%): C, 51.22; H, 2.61.

It was confirmed by $^1$H-NMR that the product was the desired compound.

Preparation of fluorescent compound (j)

2 mmol of β-diketone (j') was slowly added to 3.5 ml of stirred chlorosulfuric acid at room temperature. After this mixture was stirred at room temperature for 7 hours, the reaction mixture was carefully and slowly added dropwise to 150 ml of stirred water/ice (using external cooling with ice/water). The resulting precipitate was quickly separated by centrifugation, washed with cold water (at about 5° C.), and centrifuged twice. Using a small amount of cold water, the precipitate was transferred to a glass filter and freed of water by suction filtration. The chlorosulfonylated β-diketone so formed was vacuum-dried at room temperature for 48 hours or more. Its yields was 77%.

Elemental analysis: Calcd. (%): C, 44.76; H, 1.88. Found (%): C, 44.50; H, 1.92.

It was confirmed by $^1$H-NMR that the product was the desired compound.

Labeling of a protein with the fluorescent compound (j)

The labeling of bovine serum albumin (BSA) with fluorescent compound (j) is described below.

50 mg of BSA was dissolved in 10.00 ml of a 0.1 mol/L carbonate buffer solution (pH 9.3). Then, 2 ml of a DMF solution containing fluorescent compound (j) in the same molar amount as the amino groups present in bovine serum albumin (59 —$NH_2$ groups per molecule) was slowly added dropwise to the stirred BSA solution at room temperature. After this mixture was stirred at room temperature for an hour, the labeled BSA and the hydrolyzate of unreacted fluorescent compound were separated by gel filtration. In this separation step using a gel column (Sephadex G-50, 1.0×29.1 cm), a 0.05 mol/L aqueous solution of ammonium hydrogen carbonate (pH 8.0) was used as the developing solvent. The flow rate was 1 ml per 90 seconds and the effluent was collected as 1 ml fractions. Since a satisfactory separating effect would not be achieved by separating 10 ml of the solution at a time under these column conditions, 5 ml portions of the solution were separated. Fractions containing the labeled BSA were combined and dialyzed against water at 4° C. overnight to remove inorganic salts therefrom. Using the solution before gel filtration, its absorbance at 330 nm was measured. Then, the molar absorption coefficient at 330 nm of the fluorescent compound was calculated from the molar concentration of the fluorescent compound used and the absorbance at 330 nm. The molar absorption coefficient so calculated was $3.41 \times 10 \text{ mol}^{-1} \text{ cm}^{-1}$ L, and there was no absorption of bovine serum albumin at 330 nm. On the assumption that the molar absorption coefficient does not change during the process of the labeling reaction, the label concentration in the labeled BSA solution and the labeling ratio of BSA to label were calculated. The labeling ratio of BSA to the fluorescent compound in the labeled BSA fraction obtained in the above-described manner was about 35.

Labeling of streptavidin and avidin with fluorescent compound (j)

The labeling of streptoavidin (SA) and avidin (AD) with the aforesaid fluorescent compound (j) is described below.

To 1.5 mg of the aforesaid fluorescent compound (j) was added a solution of 5 mg of streptoavidin (or avidin) in 1.1 ml of a 0.1 mol/L carbonate buffer solution (pH 9.1) and 25 µL of DMF. After this mixture was stirred at room temperature for two hours, the insoluble matter was separated by centrifugation. The precipitate was washed with 2.0 ml of a 0.05 mol/L Tris-HCl buffer solution (pH 7.7) and centrifuged. The two supernatants were combined and dialyzed twice against 4 L of a solution containing 0.1 mol/L of $NaHCO_3$ and 0.25 g of $NaN_3$ at 4° C. (for 16 hours and for 6 hours, respectively). The labeling ratio of protein to the fluorescent compound in the labeled protein solution obtained in this manner was about 10.

Labeling of anti-mouse IqG(H+L) sheep antibody with fluorescent compound (j)

2 ml of a 2 mg/ml solution of anti-mouse IgG(H+L) sheep antibody was dialyzed twice against 3 L of physiological saline at 4° C. for 24 hours, and adjusted to pH 9.2 with a 0.5 mol/L $Na_2CO_3$ solution. Then, 2.0 mg of the aforesaid fluorescent compound (j) was added to the antibody solution and 125 µL of DMF was added thereto with stirring. After this mixture was stirred at room temperature for an hour, 50 µL more of DMF was added thereto and the resulting mixture was stirred again at room temperature for an hour. The insoluble matter was separated by centrifugation, and the supernatant was dialyzed twice against 4 L of a solution containing 0.1M $NaHCO_3$ and 0.25 g of $NaN_3$ at 4° C. for 24 hours. The labeling ratio of protein to the fluorescent compound in the labeled protein solution obtained in this manner was about 11.

It was confirmed by application to practical immunoassays that the labeled proteins obtained in the above-described manner retained their physiological activities.

Method for the measurement of fluorescence intensities and results

The method for the measurement of fluorescence intensities was the same as described above for fluorescent compound (b).

The results are shown in TABLE 12.

TABLE 12

| Fluorescent compound | $\lambda_{ex}$ (nm) | $\lambda_{em}$ (nm) | Fluorescence intensity ($10^3$ cm$^{-1}$m$^{-1}$) |
|---|---|---|---|
| LKB system (conventional technique) | 339 | 610 | 12.16 |
| j' | 340 | 610 | About 150 |

Fluorescence characteristics of a labeled BSA solution in the presence of europium(III)

The fluorescence spectrum of a $BSA(j)_n-Eu^{3+}$ solution was as follows.

In Tris-HCl: $\lambda_{ex.max}$=326 nm
  $\lambda_{em.max}$=611.6 nm (half-width, about 9 nm)
In carbonate buffer solution:
  $\lambda_{ex.max}$=324 nm
  $\lambda_{em.max}$=611.6 nm (half-width, about 9 nm)
In phosphate buffer solution:
  $\lambda_{ex.max}$=324 nm
  $\lambda_{em.max}$=611.6 nm (half-width, about 9 nm)
In topo-SDS-$NaCHO_3$* solution:
  $\lambda_{ex.max}$=334 nm
  $\lambda_{em.max}$=613.4 nm (half-width, about 9 nm)

(* A 1.0×10 mol/L topo–0.05% SDS–0.1 mol/L $NaHCO_3$ solution)

The results of measurement of the influence of pH and buffer solutions on the fluorescence intensity of the $BSA(j)_n-Eu^{3+}$ solution and of its fluorescence lifetime are shown in TABLE 13.

TABLE 13

| Buffer solution | 0.1 mol/L Tris-HCl | | | | | 0.1 mol/L carbonate | 0.1 mol/L phosphate | 1.0 × 10$^{-5}$ mol/L topo-0.05% SDS-0.1 mol/L NaHCO$_3$ |
|---|---|---|---|---|---|---|---|---|
| pH | 7.2 | 7.8 | 8.5 | 9.1 | 9.9 | 9.3 | 9.0 | 8.4 |
| Relative fluorescence intensity | 75 | 89 | 97 | 100 | 100 | 44 | 16 | 321 |
| Fluorescence lifetime | | | 261 µs | | | | | 395 µs |

*$\lambda_{ex}$ = 337 nm.
Measured solution: $BSA(j)_{35}-Eu^{3+}$, $[BSA(j)_{35}]$ = 1.8 × 10$^{-8}$ mol/L, $[Eu^{3+}]$ = 1.0 × 10$^{-6}$ mol/L.

Time-resolved fluorometry of labeled BSA solutions

Figure 3:
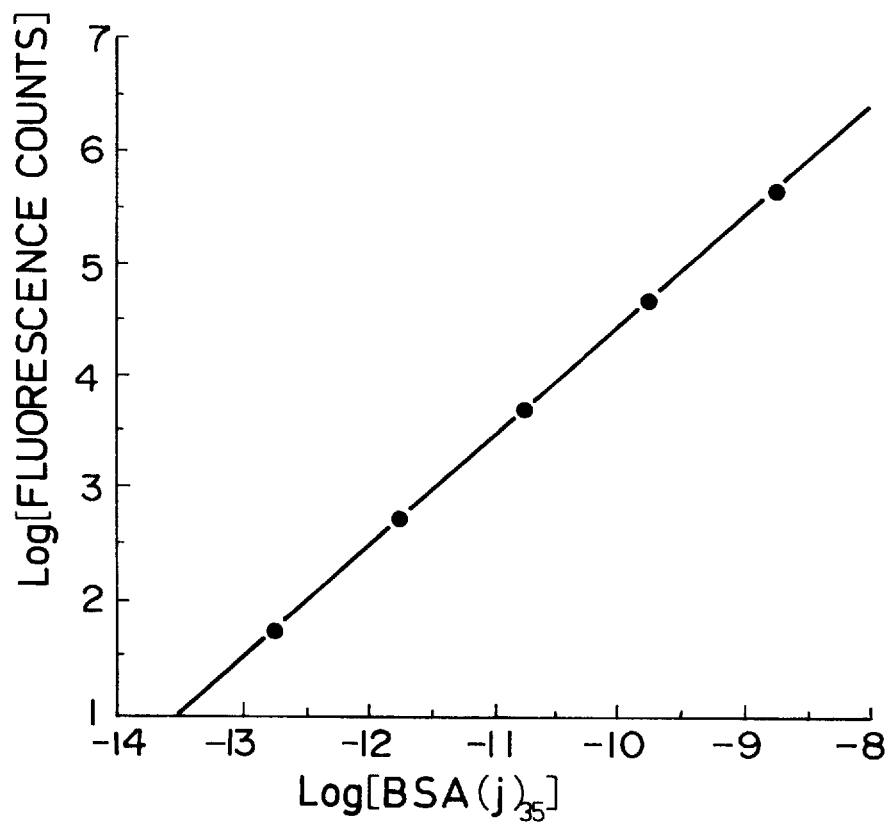
FIG. 3 is a graph in which the logarithm of the concentration (M) of a bovine serum albumin $(j)_{35}$ solution is plotted as abscissa and the logarithm of the fluorescent count as ordinate.

Using a $BSA(j)_{35}$ solution obtained as above, a 1.0×10$^{-5}$ mol/L topo–0.05% SDS–0.1 mol/L $NaHCO_3$ solution, and a 1.0×10$^{-5}$ mol/L $EuCl_3$ solution, a BSA(fluorescent compound)$_{35}$-Eu$^{3+}$ standard solution (2.8×10$^{-14}$ mol/L) was prepared. At the same time, a series of solutions were prepared by fixing the Eu$^{3+}$ concentration at 1.0×10$^{-6}$ mol/L and varying the BSA(fluorescent compound)$_{35}$ concentration. The prepared solutions were allowed to stand at room temperature for 2 hours and then subjected to time-resolved fluorometry. Measurements were made by pipetting each solution (having an identical concentration) into 4 wells (300 µl per well), and the average of the measured values was regarded as the measured value (I). Similarly, the solvent was pipetted into 4 wells and the average of the measured values was regarded as the background ($I_0$). The (I–$I_0$) values thus obtained were used as fluorescent counts to construct a working curve. The results are shown in FIG. 3. From FIG. 3, the detection limit of fluorescent compounds (j) was determined to be 1.3×10$^{-12}$ mol/L.

Using a time-resolved fluorophotometer ("Cyber Fluor 615"), the detection sensitivity of the labeled reagent of the present invention (i.e., the labeled BSA–Eu$^{3+}$) was compared with those of conventional techniques (i.e., the LKB system and an aromatic amine type labeled reagent). It can be seen from TABLE 14 that the labeled reagent of the present invention is several tens of times as sensitive as the LKB system and several thousand times as sensitive as the aromatic amine type labeled reagent using BCPDA as the fluorescent compound.

TABLE 14

| | Detection limit of fluorescent compound (mol/L) |
|---|---|
| LKB system | 5.0 × 10$^{-11}$ |
| BCPDA | 1.0 × 10$^{-8}$ |
| j | 1.3 × 10$^{-12}$ |

Time-resolved fluoroimmunoassay of human alpha-fetoprotein (AFP) using polyclonal antibodies and SA-BHHCT–Eu$^{3+}$ label Labeling of streptavidin with the fluorescent compound (j)

To 1.5 mg of the fluorescent compound (j) (BHHCT) was added a solution of 5 mg of streptavidin (SA) in 1.1 ml of a 0.1 mol/L carbonate buffer (pH 9.1) and 25 μL of DMF solution. After this mixture was stirred at room temperature for 2 to 4 hours, the insoluble matter was separated by centrifugation. The precipitate was washed with 2 ml of a 0.05 mol/L Tris-HCl buffer solution (pH 7.8) and centrifuged. The two supernatants were combined and dialyzed against 4 L of a solution containing 0.1 mol/L of NaCHO₃ and 0.25 g of NaN₃ at 4° C. twice (for 16 hours and for 6 hours, respectively). After dialyzation, a small amount of insoluble matter was removed by centrifugation. 10 mg of bovine serum albumin (BSA) and 2 mg of NaN₃ were added to the labeled SA solution. The labeled SA solution was adjusted to about pH 6.0 to 6.5 with 0.1 mol/L of HCl. The volume of the obtained solution was about 4 ml. The solution was cloudy, but was preserved as it was. The solution was divided into 100 μL portions and was preserved at −20° C. Before the labeled SA was used in immunoassay, its solution was diluted to one three hundredth (1/300) of the original concentration with a 0.05 mol/L of Tris-HCl (pH 7.8) solution which contains 1% of BSA, 0.9% of NaCl, 0.05% of NaN₃ and $1.0\times10^{-6}$M of EuCl₃, was allowed to stand overnight at 4° C. or heat at 50° C. for two hours and thereafter was used. Little change was observed after the diluted solution was preserved for two weeks at 4° C. The labeled SA could be preserved for a long period of time when it was preserved at −20° C.

Time-resolved fluoroimmunoassay

The fraction of anti-human AFP goat IgG was diluted with a 0.1 mol/L of carbonate buffer solution (pH 9.6) to decrease the concentration of the antibody to 2.5 μg/ml. The obtained solution was pipetted into 96 wells of a microtiter plate (100 μl per well) and was allowed to stand overnight at 4° C. The solution was removed by suction. The wells were washed with a 0.01 mol/L of phosphate buffer-0.05% of Tween 20 solution twice and with a 0.01 mol/L of phosphate buffer solution (pH 7.4) once. A 1% of BSA-2% of sucrose-0.05% of NaN₃-0.1 mol/L of NaHCO₃ buffer solution (pH=8.3) was pipetted into the wells (100 μL per well), was allowed to stand at room temperature for an hour and was washed with the above-described phosphate buffer solution. These steps are a coating step and a blocking step of wells. The plate could be preserved for a long period of time (for example, one and a half months) at −20° C.

Human AFP standard solution was diluted with a 1% of BSA-0.05% of NaN₃-0.9% of NaCl-0.01 mol/L of phosphate buffer (pH 7.4) solution to a series of solutions with concentrations ranging from $10^4$ ng/ml to $10^{-6}$ ng/ml. The diluted solutions were pipetted into the wells (50 μl per well) and were incubated for an hour at 37° C. The solutions were removed by suction, and the wells were washed with phosphate buffer. Rabbit anti-human AFP IgG solution, which had been diluted to one five hundredth (1/500) of the original concentration with a 1% of BSA-0.05% of NaN₃-0.9% NaCl-0.01 mol/L of phosphate buffer solution, was pipetted into the wells (50 μl per well) and was allowed to stand for an hour at 37° C. After the solution was removed by suction and the wells were washed, a biotinylated goat anti-rabbit IgG (H+L) solution which had been diluted to one hundredth (1/100) of the original concentration was pipetted into wells (50 μl per well) and was allowed to stand for an hour at 37° C. After the solution was removed and the wells were washed with a physiological saline (NaCl)-0.05% of Tween 20 solution twice and with a physiological saline solution once, the SA-BHHCT-Eu³⁺solution was pipetted into the wells (50 μl per well) and was allowed to stand for an hour at 37° C.

Figure 4:
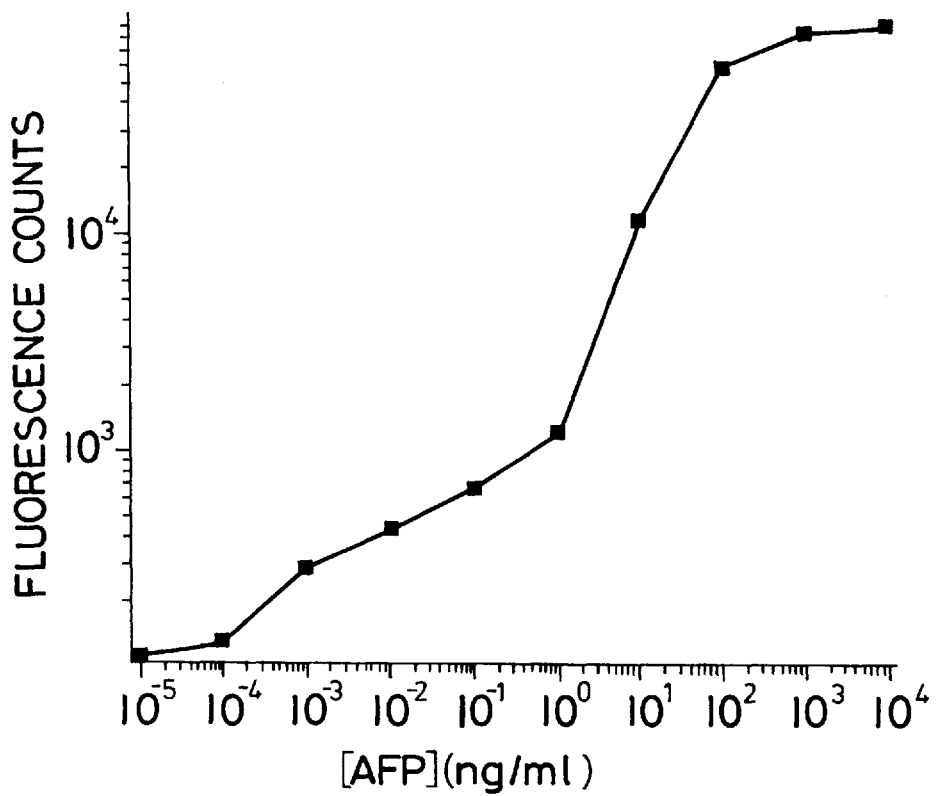
FIG. 4 is a graph of solid-phase measurements in which the logarithm of the concentration of AFP is plotted as abscissa and the logarithm of the fluorescence counts as ordinate.
Figure 5:
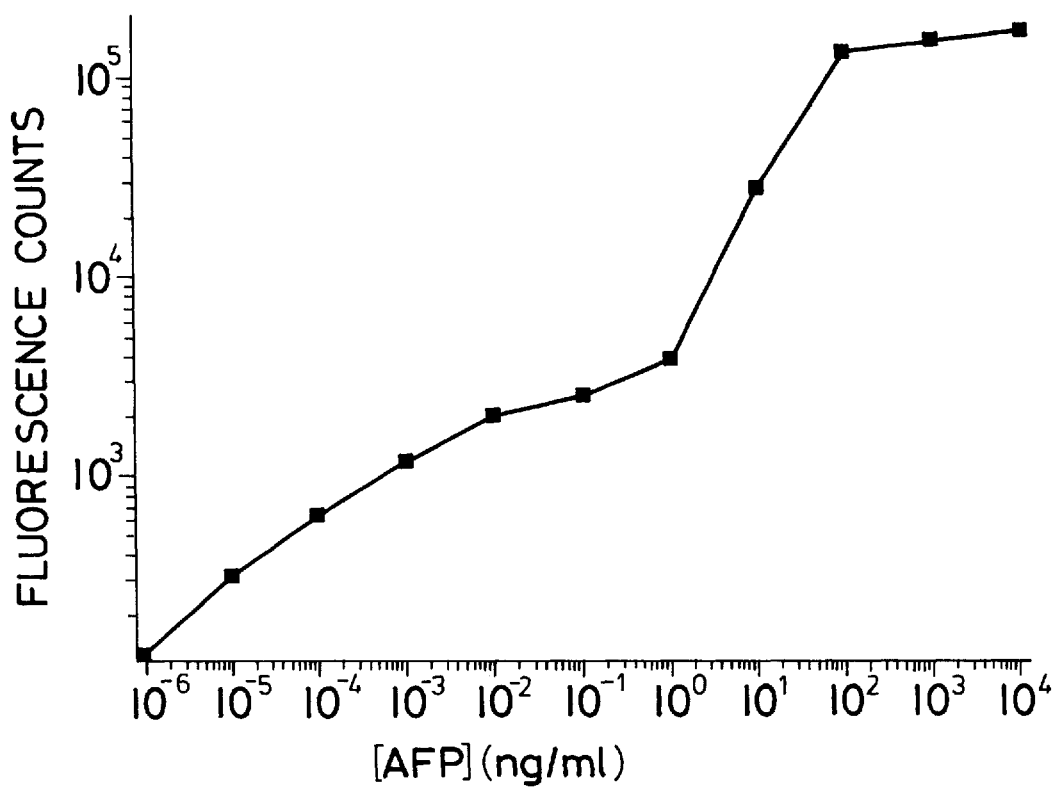
FIG. 5 is a graph of measurements after dissolution in which the logarithm of the concentration of AFP is plotted as abscissa and the logarithm of the fluorescence counts as ordinate.

After the solution was removed and the wells were washed with a physiological saline-0.05% of Tween 20 solution three times and with a 0.1 mol/L of Tris-HCl-0.05% of Tween 20 solution (pH=8.5) five times, the solid-phase measurements of the fluorescence were made. A $1.0\times10^{-5}$ mol/L of topo-0.05% of SDS-$1.0\times10^{-6}$ mol/L of EuCl₃-0.1 mol/L of NaHCO₃ solution was pipetted into the wells (50 μl per well) and was allowed to stand for an hour at 50° C. When the temperature of the solution reached to room temperature, the fluorescence of the solution was measured. The results of the solid-phase measurements are shown in FIG. 4. The results of the measurements after dissolution are shown in FIG. 5.

Sensitivity of AFP immunoassay using SA-BHHCT-Eu³⁺

The detection limit in solid-phase measurements was $10^{-5}$ ng/ml. It corresponds to $1.4\times10^{-16}$ mol/L or $7.1\times10^{-21}$ mol/assay (50 μl). The detection limit after dissolution was $10^{-6}$ ng/ml. It corresponds to $1.4\times10^{-17}$ mol/L or $7.1\times10^{-22}$ mol/assay (50 μl). The coefficient of variation in measurements was less than 10%. The detection limit of AFP immunoassay using conventional horse radish peroxidase (HRP)-avidin was 1 ng/ml.

We claim:

1. A fluorescent compound of the general formula

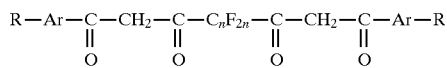

where R is a group capable of combining with proteins, Ar is a conjugated double bond system, and n is a whole number.

2. A fluorescent compound of the general formula

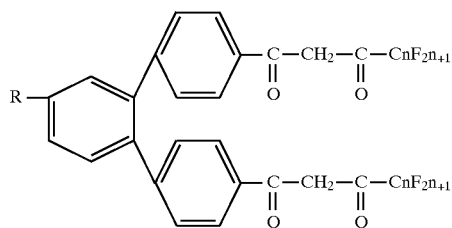

where R is a group capable of combining with proteins, and n is a whole number.

3. A labeling reagent for use in immunoassays which contains a fluorescent compound as claimed in claim 1.

4. A labeling reagent for use in immunoassays which contains a fluorescent compound as claimed in claim 2.

5. A fluorescent compound of the general formula

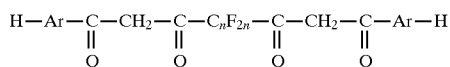

where Ar is a conjugated double bond system, and n is a whole number.

6. A fluorescent compound of the general formula

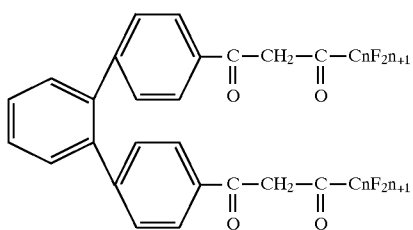

where n is a whole number.

7. A fluorescent compound of the general formula

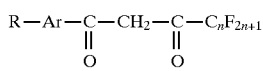

where R is a group selected from the group consisting of $ClSO_2$— and S=C=N—, Ar is a conjugated double bond system selected from the group consisting of

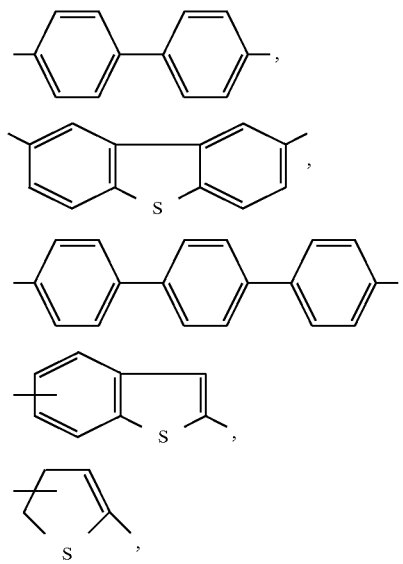

and n is a whole number which is at least 2.

8. A labeling reagent for use in immunoassays which contains a fluorescent compound as claimed in claim 7.

9. A fluorescent compound of the general formula

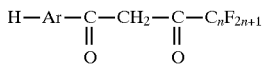

where Ar is a conjugated double bond system selected from the group consisting of

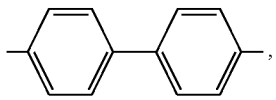

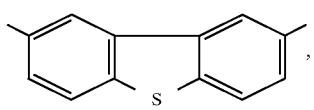

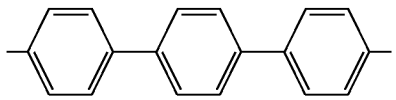

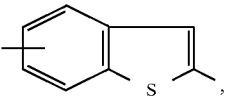

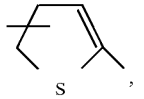

and n is a whole number which is at least 2.

* * * * *

UNITED STATES PATENT AND TRADEMARK OFFICE
CERTIFICATE OF CORRECTION

PATENT NO. : 5,859,297

DATED : January 12, 1999

INVENTOR(S) : Matsumoto et al.

It is certified that error appears in the above-identified patent and that said Letters Patent is hereby corrected as shown below:

On the title page, Item

[30] Foreign Application Priority Data, "Aug. 3, 1996" should read --Mar. 8, 1996--.

[56] References Cited, FOREIGN PATENT DOCUMENTS, "1/1992" should read --10/1992--.

Signed and Sealed this

Eighth Day of June, 1999

Attest:

Q. TODD DICKINSON

*Attesting Officer*   *Acting Commissioner of Patents and Trademarks*